(12) United States Patent
Gougeon et al.

(10) Patent No.: US 12,370,131 B2
(45) Date of Patent: Jul. 29, 2025

(54) COMPOUND COMPRISING A FUNCTIONAL AGENT, AND RELATED MANUFACTURING METHOD

(71) Applicant: MIYOSHI EUROPE, Saint-Priest (FR)

(72) Inventors: Sébastien Gougeon, Saint-Priest (FR);
Quentin Dauphin, Saint-Priest (FR);
Laetitia Sellal, Saint-Priest (FR);
Stephane Nicolas, Saint-Priest (FR);
Pauline Bosmet, Saint-Priest (FR)

(73) Assignee: MIYOSHI EUROPE, Saint-Priest (FR)

( * ) Notice: Subject to any disclaimer, the term of this patent is extended or adjusted under 35 U.S.C. 154(b) by 813 days.

(21) Appl. No.: 17/606,402

(22) PCT Filed: Apr. 23, 2020

(86) PCT No.: PCT/FR2020/050689
§ 371 (c)(1),
(2) Date: Oct. 25, 2021

(87) PCT Pub. No.: WO2020/217022
PCT Pub. Date: Oct. 29, 2020

(65) Prior Publication Data
US 2022/0192933 A1    Jun. 23, 2022

(30) Foreign Application Priority Data
Apr. 26, 2019 (FR) ..................... 1904459

(51) Int. Cl.
*A61K 8/02* (2006.01)
*A61K 8/06* (2006.01)
(Continued)

(52) U.S. Cl.
CPC .......... *A61K 8/0287* (2013.01); *A61K 8/064* (2013.01); *A61K 8/19* (2013.01); *A61K 8/29* (2013.01);
(Continued)

(58) Field of Classification Search
None
See application file for complete search history.

(56) References Cited

U.S. PATENT DOCUMENTS 4,235,641 A    11/1980    Engelmann et al.
4,464,203 A    8/1984    Belde et al.
(Continued)

FOREIGN PATENT DOCUMENTS

CN    104059273 A    9/2014
FR    2474520 A1    7/1981
(Continued)

OTHER PUBLICATIONS

International Search Report dated Sep. 17, 2020 issued in corresponding International Application No. PCT/FR2020/050689.

*Primary Examiner* — Gina C Justice
(74) *Attorney, Agent, or Firm* — Nath, Goldberg & Meyer; Joshua B. Goldberg

(57) ABSTRACT

The invention relates to a compound (1) comprising at least 50% by weight of a functional agent, characterized in that it also comprises a waxy matrix (3), within which said functional agent is dispersed, wherein said compound (1) is solid at room temperature and intended to be dispersed by fluidization and/or solubilization within a cosmetic and/or dermatological composition to incorporate therein said functional agent, said functional agent being formed from solid particles (2) having undergone a surface treatment resulting in a reductions in the absorption capacity of the waxy matrix (3) by said treated solid particles (2), as compared to untreated solid particles of the same nature. The invention also relates to a formulation of cosmetic and/or dermatological compositions.

21 Claims, 1 Drawing Sheet

(51) Int. Cl.
  *A61K 8/19*   (2006.01)
  *A61K 8/29*   (2006.01)
  *A61Q 1/06*   (2006.01)
  *A61Q 1/12*   (2006.01)
  *C09C 1/24*   (2006.01)
  *C09C 1/36*   (2006.01)
  *C09C 3/12*   (2006.01)

(52) U.S. Cl.
  CPC .............. *A61Q 1/06* (2013.01); *A61Q 1/12* (2013.01); *C09C 1/24* (2013.01); *C09C 1/3684* (2013.01); *C09C 3/12* (2013.01); *A61K 2800/43* (2013.01); *A61K 2800/612* (2013.01); *C01P 2004/61* (2013.01); *C01P 2004/62* (2013.01); *C01P 2004/64* (2013.01)

(56) References Cited

U.S. PATENT DOCUMENTS

| | | | |
|---|---|---|---|
| 6,316,547 | B1 | 11/2001 | Varlet |
| 6,482,441 | B1 | 11/2002 | Hasegawa et al. |
| 2002/0151639 | A1 | 10/2002 | Knebelkamp et al. |
| 2006/0263547 | A1* | 11/2006 | Cojocariu ............ G02B 5/0242 428/1.33 |
| 2009/0148393 | A1* | 6/2009 | Maitra ................... A61K 8/88 424/63 |
| 2011/0088595 | A1* | 4/2011 | Wilhelm ............... C09C 1/0015 106/400 |
| 2014/0005316 | A1 | 1/2014 | Thetford et al. |
| 2018/0369083 | A1* | 12/2018 | Valverde ................ A61K 8/37 |

FOREIGN PATENT DOCUMENTS

| | | |
|---|---|---|
| GB | 906973 A | 9/1962 |
| JP | H6-93201 A | 4/1994 |

* cited by examiner

COMPOUND COMPRISING A FUNCTIONAL AGENT, AND RELATED MANUFACTURING METHOD

This is a National Phase Application filed under 35 U.S.C. 371 as a national stage of PCT/FR2020/050689, filed Apr. 23, 2020, an application claiming the benefit of French Application No. 1904459, filed Apr. 26, 2019, the content of each of which is hereby incorporated by reference in its entirety.

TECHNICAL FIELD

The present invention relates to the general technical field of substances and compounds used in the field of formulation of cosmetic and/or dermatological compositions, in particular of the kind of compounds including a functional agent, for example of the pigment type.

More particularly, the present invention concerns a compound comprising at least 50 weight % of a functional agent.

The present invention also concerns a method for producing such a compound.

Finally, the present invention concerns a method for producing a cosmetic and/or dermatological composition.

PRIOR ART

The production of cosmetic and/or dermatological compositions usually require combining some substances and compounds to be mixed into a homogeneous material, that is to say which has a regular distribution of the different compounds and substances, and which is stable, namely in particular without separation of the phases over time, for example by sedimentation or creaming, or another undesirable phenomenon such as coalescence or flocculation.

To this end, it is known to resort to solid pigments which are ground into fine particles by grinding units, before being integrated into a cosmetic composition to color or enhance its matt or shiny appearance. Although it they are generally satisfactory in their final use, the implementation of these ground pigments still has some drawbacks.

One major drawback of the use of these ground pigments in making of a cosmetic composition lies in the pulverulent nature of these, which makes storage, transport and handling of these ground pigments complex, expensive, dirty, and even polluting, while featuring a non-negligible risk regarding the safety of living beings and installations, as well as major difficulties with regards to cleaning and/or elimination of these ground pigments. In general, the finer the grinding of the pigments and therefore the smaller the pigment particles, the more complex the management will be. Moreover, the powdery state of these pigments confers a large specific surface (actual surface/low mass) thereon resulting, in turn, in a considerable reactivity, and therefore in particular in an increased risk of degradation over time, and even a risk of accident, such as an explosion in particular.

In addition, grinding units are quite often specialized and very expensive, whereas the grinding process itself could turn out to be particularly long and complex depending on the nature and desired size of the ground pigment particles, which could vary for example according to aesthetics, organoleptic and/or qualitative requirements. In most cases, because of their cost and their complexity, these grinding units are not specifically dedicated to the specific grinding of a pigment, and therefore require settings to grind a pigment according to other specifications, such as a different grain-size, or to grind other types of pigments. Thus, these grinding units process different «batches» or sets of several types and sizes of ground pigments that shall be stored, transported and used afterwards at different cosmetic compositions production units. This results, on the one hand, in a multiplication of batches of pulverulent pigments that are difficult to deal with (storage, transport, handling in particular during mixing with other substances to make the formulation of a cosmetic composition, avoiding mixing of different pigments), and, on the other hand, in the fact that the cosmetic compositions production units are almost always distinct and remote from the grinding units, which complicates even more the management (in particular the transport) of the ground pigments.

Ultimately, the integration of the ground pigments into the cosmetic compositions, as currently practiced, is insufficient in terms of ease of implementation, storage, transport, safety, and costs.

DISCLOSURE OF THE INVENTION

Consequently, the invention proposes overcoming the different drawbacks set out hereinbefore by providing a new compound which not only turns out to be capable of being easily integrated into a cosmetic and/or dermatological composition, but further has a great ease of implementation with regards to management thereof and in particular transport, storage and handling thereof.

Another object of the invention aims at providing a new compound with an extremely simple and cheap design.

Another object of the invention aims at providing a new compound that is particularly easy to handle.

Another object of the invention aims at providing a new compound that is particularly easy to transport and to store.

Another object of the invention aims at providing a new compound that is easy to effectively integrate to cosmetic and/or dermatological compositions.

Another object of the invention aims at providing a new compound whose deign enables it to obtain a good repeatability as a component for the formulation of cosmetic and/or dermatological compositions.

Another object of the invention aims at providing a new compound whose design enables it to be used in a wide range of applications, in particular for a very wide variety of cosmetic and/or dermatological compositions.

Another object of the invention aims at providing a new compound having a minimal risk with regards to safety of living beings and which does not degrade the installations.

Another object of the invention aims at providing a new compound whose manufacture can be easily industrialized, implementing a minimum number of different substances.

Another object of the invention aims at providing a new compound that degrades only very little, or not at all, over time.

Another object of the invention aims at providing a method for producing a compound whose implementation is simple, easy and cost-effective, and has a good repeatability and a good safety for the user.

Another object of the invention aims at providing a method for producing a cosmetic and/or dermatological compound whose implementation is rapid, easy to monitor and easy, while guaranteeing optimum safety conditions.

The objects assigned to the invention are achieved by means of a compound comprising at least 50 weight % of a functional agent, characterized in that it also comprises a waxy matrix within which said functional agent is dispersed, said compound being solid at room temperature and intended to be dispersed by fluidification and/or solubilization within a cosmetic and/or dermatological composition to integrate said functional agent therein, said functional agent being formed by solid particles having undergone a surface treatment causing a reduction of the capacity of absorption of the waxy matrix by said treated solid particles, in comparison with non-treated solid particles of the same kind.

The objects assigned to the invention are also achieved by means of a method for producing a compound comprising at least 50 weight % of a functional agent, characterized in that it comprises at least:
- a step of heating up a waxy matrix in order to obtain a fluid matrix,
- a step of treating solid particles during which these undergo a surface treatment causing a reduction of the capacity of absorption of the fluid matrix by the treated solid particles, in comparison with non-treated solid particles of the same kind, said treated solid particles forming said functional agent,
- a step of dispersing said functional agent within said fluid matrix, said compound being solid at room temperature and intended to be dispersed by fluidification and/or solubilization within a cosmetic and/or dermatological composition to integrate said functional agent therein.

The objects assigned to the invention are further achieved by means of a method for producing a cosmetic and/or dermatological composition comprising a redispersion step during which a compound as mentioned hereinbefore is added and then mixed with one or several cosmetically and/or dermatologically acceptable component(s).

BRIEF DESCRIPTION OF THE DRAWINGS

Other particularities and advantages of the invention will appear and come out in more detail upon reading the description made hereinafter, with reference to the appended drawings, provided as merely illustrative and non-limiting examples, wherein.

BEST WAY TO IMPLEMENT THE INVENTION

Figure 1:
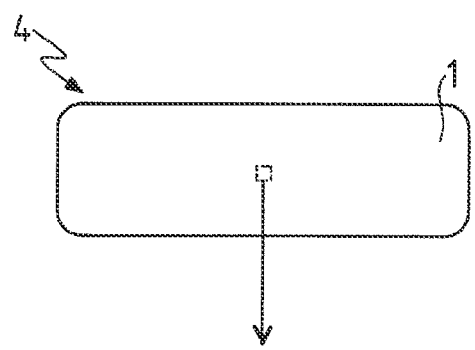
FIG. 1 schematically illustrates, according to a side view, an example of a compound according to the invention, which, in this instance, is in the form of a stick obtained by extrusion.

As illustrated in the figures, the invention concerns a compound 1. Hence, said compound 1 is preferably formed by several different elements, more specifically by a relatively homogeneous and stable mixture of several different substances, materials, matters together, advantageously all cosmetically and/or dermatologically acceptable, that is to say suited to be integrated within a cosmetic and/or dermatological composition. Hence, the compound 1 advantageously has a very low, and possibly zero, toxicity level with regards to the use of a cosmetic and/or dermatological composition. Thus, according to the invention, the compound 1 comprises at least 50 weight % of a functional agent. According to a preferred embodiment, the compound 1 comprises (strictly) more than 50 weight %, preferably (strictly) more than 60 weight %, more preferably at least 70 weight %, still more preferably at least 80 weight %, even more preferably at least 85 weight %, still more preferably at least 90 weight %, of said functional agent. Advantageously, said functional agent is selected appropriately, so as to form an element suited to be integrated within a cosmetic and/or dermatological composition. Thus, a high proportion of the functional agent within the compound 1 is particularly advantageous when the latter constitutes an intermediate (or possibly almost finite) product intended to be redispersed with other compounds to form a finite cosmetic and/or dermatological product, as it will be described in more detail hereinafter. Indeed, said compound 1 advantageously serves as an intermediate «support» or «vehicle» for the functional agent, and it is therefore preferable that the proportion of the functional agent within the compound 1 is as high as possible on the one hand for the final formulation (that is to say the finite cosmetic and/or dermatological product) not to depend or depend very little on the nature of the substances other than said functional agent within said compound 1, and on the other hand for obvious reasons relating to costs, storage and transport, an intermediate compound having a low content of the functional agent which, by definition, has to be used in a larger amount and therefore occupying a larger volume for a generally greater weight for a given amount of the functional agent, whereas the substances other than said functional agent within said compound 1, being in greater proportions, represent a high cost that what is more is not valued in the final formulation (and possibly «parasitize» said final, or finite cosmetic and/or dermatological, formulation). Preferably, said functional agent is intended to fill one or several very specific function(s) within a cosmetic and/or dermatological composition. For example, said functional agent is intended to form a physical sunscreen, in particular within a sun cream type cosmetic and/or dermatological composition, that is to say it is intended to form a physical, preferably opaque, barrier between the Sun's ultraviolet rays and the skin of a user of said cosmetic and/or dermatological composition.

According to the invention, said functional agent is formed by solid particles 2, that is to say which are preferably solid at least at room temperature, and even solid at higher temperatures, such as for example between 30 and 90° C. Preferably, said solid particles are insoluble in water. Preferably, said solid particles have an average size comprised between 10 nm and 500 µm, preferably between 100 nm and 100 µm. Hence, said average size preferably refers to the average grain-size of said particles 2, and in particular their average diameter or an average maximum dimension of said particles, which could be measured in particular using only one sample of said particles.

For example, said solid particles 2 comprise at least organic and/or mineral (that is to say inorganic) pigments, organic and/or mineral charges, composite and/or biocomposite materials, or a mixture of these. According to a particular embodiment, said solid particles 2 are primarily, or totally, formed by mineral pigments, which could be constituted for example by titanium dioxide, iron oxide(s), chromium oxide(s), ultramarine pigment(s) (for example ultramarine blue or violet), tin oxide(s) and/or zinc oxide. For example, said organic pigments are constituted by carbon black and/or organic lacquers. For example, said mineral charges are constituted by talc, mica, sericite, kaolin, silica, hydroxyapatite, barium sulfate, perlite, calcium carbonate, and/or borosilicates. For example, said organic charges are constitutes by starch, cellulose, natural or synthetic polymers, and/or silicone polymers and resins. For example, said composites and/or biocomposites include one or several mother-of-pearl(s). In the case where said solid particles consist of pigments, the functional agent is for example intended to color a cosmetic and/or dermatological formulation, or to protect the skin from the Sun (case of the aforementioned sun cream, the solid particles 2 forming in particular a sunscreen). In the case where said solid particles 2 consist of charges, the functional agent may for example be intended to modify the organoleptic properties of a cosmetic and/or dermatological formulation.

Still according to the invention, the compound 1 also comprises a waxy matrix 3 within which said functional agent is dispersed. In other words, said functional agent, and more specifically said solid particles 2, is/are advantageously mixed with said waxy matrix 3 and scattered within the latter, preferably homogeneously, that is to say according to a regular volumetric distribution. Advantageously, within the compound 1, the waxy matrix 3 and said solid particles 2 form, from a macroscopic perspective, one single phase, and it is impossible to differentiate the waxy matrix 3 from said solid particles 2 with the naked eye.

For example, said waxy matrix 3 comprises at least one natural, mineral and/or synthetic, wax, a fatty body solid at room temperature derived from fractioning of one or several natural and/or synthetic oil(s), a natural and/or synthetic resin, a silicone or silicone polymer wax, an organosilicon (or organosilicic) material or a mixture of these. For example, said organosilicon material (or a plurality of different organosilicon materials) belongs to the family of silsesquioxanes, which have the general formula $(RSiO_{3/2})_n$, R representing a carbonated group in particular of the alkane, alkene, aryl or arylene type, whereas as usual Si represents a silicon atom, and O represents an oxygen atom, n representing an integer generally greater than 1, for example comprised between 3 and 20, such as equal to 8. Advantageously, the organosilicon material is a silsesquioxane polymer. According to a particular embodiment of the invention, said waxy matrix 3 comprises polymethylsilsesquioxane, and is for example primarily formed by the latter. The polymethylsilsesquioxane is a type of organosilicon materials particularly effective when it is used as a waxy matrix 3. According to other particular embodiments, the waxy matrix 3 comprises, primarily (in weight) or not, cyclopentasiloxane, at least one (C30 to C45) alkyl methicone and/or hydrogenated esters such as hydrogenated esters of plant oils, for example an olive oil hydrogenated ester with the INCI name «Hydrogenated olive oil stearyl esters». Of course, said waxy matrix 3 may possibly be formed by a mixture of several substances, in particular among those mentioned hereinbefore. Preferably, said organosilicon material is an organosilicon material. Preferably, said waxy matrix 3 is substantially solid at room temperature, and in particular below 30° C., preferably below 45° C., more preferably below 55° C., even more preferably below 65° C. Conversely, said waxy matrix 3 is advantageously substantially fluid at a temperature higher than room temperature, and for example a temperature equal to or higher than 30° C., preferably 45° C., more preferably 55° C., and even more preferably 65° C. Thus, advantageously, said waxy matrix 3 has a melting point and/or a softening point comprised between 30 and 150° C. included, more preferably between 45 and 130° C. included, even more preferably between 55 and 130° C. included. In some embodiments of the invention, said waxy matrix 3 has a melting point and/or a softening point comprised between 55 and 150° C. included, for example between 55 and 95° C. included, or between 95 and 150° C. included. For example, said waxy matrix 3 has a density comprised approximately between 0.80 and 1.5, preferably between 0.9 and 1.3, for example about 1.24 in the case where the waxy matrix 3 is primarily, or totally, formed by polymethylsilsesquioxane. For example, in particular when said waxy matrix 3 is primarily, or totally, formed by polymethylsilsesquioxane, its softening point is advantageously comprised between 55 and 150° C., or between 75 and 90° C. Preferably, said waxy matrix 3 is formed by a material having general physical characteristics similar or equivalent to those of waxes, and in particular a material that significantly fluidize above a given temperature, that is to say a material that loses its solidity or switches from a very high viscosity to a much lower viscosity when it is heated up to a given temperature, or above. For example, said waxy matrix 3 is formed by a substantially heat-meltable and/or thermoplastic material, and significantly softens and/or melts when it is heated up or above a given temperature, for example 65° C. Hence, said waxy matrix 3 is preferably solid at room temperature and preferably becomes substantially fluid when it is brought to a given temperature above the room temperature, in particular above its melting and/or softening point. Advantageously, the waxy matrix 3 may be formed, at room temperature, by solid granulates distinct from each other, that is to say difficult to compact or non-compactable by mechanical pressure. It is particularly advantageous that said waxy matrix 3 is solid at room temperature, because this is preferably what will enable the compound 1 to remain, in turn, in a solid form at room temperature, said waxy matrix 3 possibly determining the physical behavior of the compound 1 in particular when said function agent is, itself, formed by a solid substance at room temperature.

Figure 3:
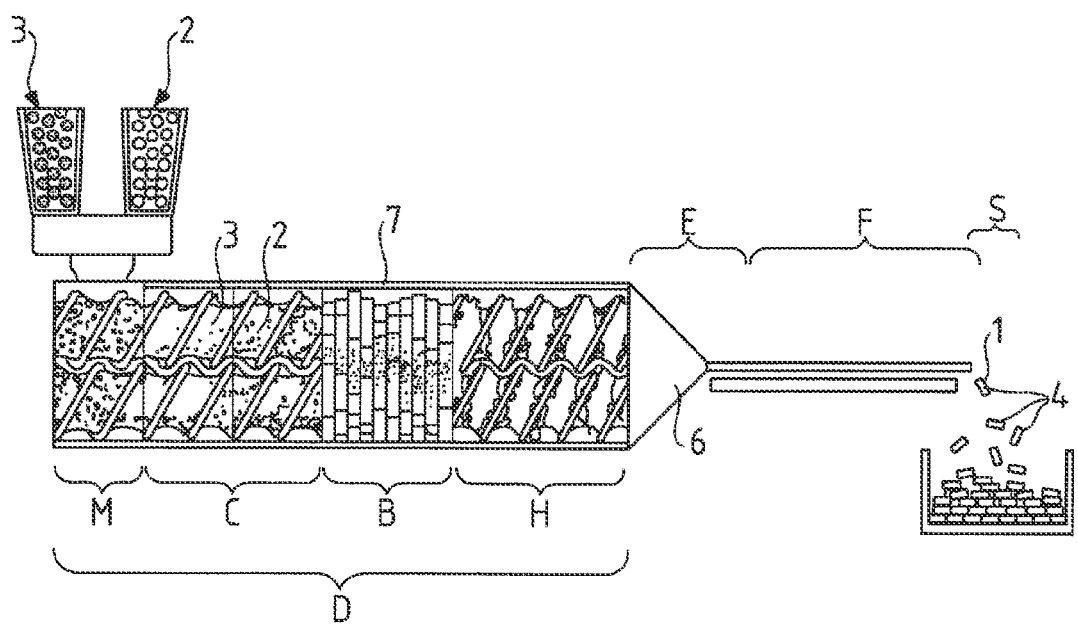
FIG. 3 schematically illustrates, according to a side view, a portion of an example of production equipment enabling the implementation of a method for producing a compound according to the invention, according to a particular embodiment implementing an extrusion step.

According to the invention, said compound 1 is solid at room temperature and intended to be dispersed by fluidification and/or solubilization within a cosmetic and/or dermatological composition to integrate said functional agent therein. Advantageously, the compound 1 has, at room temperature or below 30° C. or below 45° C. for example, a relatively firm, non-flabby, consistence, that is to say a minimum mechanical strength, substantially differentiating it from a fluid and in particular from a liquid. For example, said compound 1 is in the form of granulates, for examples pellets or sticks 4, obtained by extrusion, as illustrated in FIGS. 1 and 3. Preferably, said compound 1 is intended to be integrated or incorporated within a cosmetic and/or dermatological composition during formulation (that is to say during production). In other words, the compound 1 is advantageously intended to be mixed, preferably homogeneously, with cosmetically and/or dermatologically acceptable components, to form a cosmetic and/or dermatological composition. Advantageously, the incorporation of the compound 1 within a cosmetic and/or dermatological composition is, as it will be shown in more detail later on with the method, carried out by either one of the following actions:

through fluidification, obtained by heating, of said compound 1, that is to say a loss of the solid nature of said compound 1, generally through a softening or a melting (at least partial, since the solid particles advantageously do not fluidize) of the latter and/or of the waxy matrix 3; the subsequent mixing of the fluidized compound 1 («at hot temperature») with cosmetically and/or dermatologically acceptable components to form a cosmetic and/or dermatological composition could be facilitated because said components are advantageously primarily in the fluid form too («at hot temperature» too or not);

through solubilization of said compound 1, by one or several cosmetically and/or dermatologically acceptable components, to form a cosmetic and/or dermatological composition, these compositions being preferably primarily in the fluid form, at least one of these compounds being capable of solubilizing said compound 1, in particular even when the latter is «at low temperature» (that is to say at room temperature, in particular around 20° C. or below 30° C.), of course said compound 1 may possibly be «at hot temperature» (in this case, we will rather talk about mixing by fluidification as described hereinbefore, a combination of fluidification and solubilization being of course possible). According to a non-limiting embodiment provided only for illustration, the compound 1 comprises a waxy matrix 3 primarily formed by a silicone wax, which is easily dissolved by cosmetically and/or dermatologically acceptable components, in particular of the oil type, said compound 1 then being also advantageously easy to dissolve in said cosmetically and/or dermatologically acceptable components to form a cosmetic and/or dermatological compound.

Said cosmetic and/or dermatological composition may be intended directly to one user, or form an intermediate product which, in turn, is intended to integrate a cosmetic and/or dermatological product which, in turn, is a final one, intended to a user, or an intermediate one.

Said compound 1, advantageously resulting from mixing of the functional agent, that is to say the particles 2, and of the waxy matrix 3, is not preferably pulverulent, but cohesive and easy to «redisperse» within a cosmetic and/or dermatological composition during formulation in the fluid form. Hence, at low temperature, that is to say at room temperature, the compound 1 advantageously constitutes a solid dispersion, in the same manner as a set of solid particles 2 dispersed within the waxy matrix 3 which is also solid at low temperature. Preferably, such a configuration allows in particular getting rid of the constraints related to the nature, often naturally pulverulent, of said solid particles 2 alone. Thus, preferably, the compound 1 is substantially easier to manage, that is to say to store, transport and handle, than said particles 2 alone, in particular because the compound 1 is, for example, at room temperature, in the form of small solids (for example pellet or stick 4 type granulates), coherent, relatively inert, and easy to handle, whereas, on the contrary, said particles 2, when they are alone, often have an extremely fractioned, powdery nature, with a high reactivity and highly dispersible in air. Advantageously, the compound 1 is formed, at room temperature, by solids distinct from each other, preferably with a reduced size such as granulates, for example sticks, pellets 4, said distinct solids being preferably difficult to compact or non-compactible by mechanical pressure. Thus, said compound 1 is easy to store and easy to transport, in the form of said (small) distinct solids stockpiled in containers, for example bags, of several kilograms or several tens of kilograms (at least), without said distinct solids being detached from each other, for example by agglomeration, by coalescence, by squeezing, or by sedimentation. In other words, said compound 1 is preferably easy to store and transport in the form of said distinct solids, which remain distinct from each other during transport and/or storage, even when this/these is/are performed using containers such as bags each weighting, with their content (formed by said distinct solids, several kilograms or several tens of kilograms. Preferably, the distinct solids, formed by the compound 1 remain easy to handle even after having been stored and/or transported within said containers, and that being so thanks to the absence of attachment of said distinct solids even when they are stockpiled, said distinct solids preserving their respective unit nature despite stockpiling. Of course, the above-described transport is preferably carried out at room temperature or at a temperature slightly hotter than room temperature, but which advantageously remains below the melting and/or softening point of said waxy matrix 3. Thus, the compound 1 is practical not only to transport and store, but also to quantify when it should be dispersed within a cosmetic and/or dermatological composition, said distinct solids, and in particular the granulates (for example pellets or sticks 4). In particular, this allows quantifying easily the amount of functional agent to be obtained in the final cosmetic and/or dermatological composition, which implies an excellent repeatability when formulating the latter thanks to the compound 1.

According to the invention, said solid particles 2 have undergone a surface treatment causing a reduction of the capacity of absorption of the waxy matrix 3 by said treated solid particles 2, in comparison with non-treated solid particles of the same kind. In other words, said solid particles 2, which form the functional agent of the compound 1, have advantageously undergone a surface treatment allowing «saturating» them more rapidly with the waxy matrix 3, that is to say using a smaller amount of the waxy matrix 3 in comparison with a considered amount of solid particles 2. For example, the absorption limit (or «saturation») of the waxy matrix 3 with an amount of solid particles 2 (whether treated or not) is tested as follows: an amount (more than necessary) of the waxy matrix 2 is heated up so as to fluidize, for example heated up to 65°, and its added drop-by-drop to a considered amount of solid particles 2 (whether treated or not), which hare preferably subjected at the same time to a mixing or trituration action; the mixed or triturated solid particles 2/drops of waxy matrix 3 mixture will firstly form an extremely viscous, and even solid or almost solid, paste, in the same manner as for example a plasticine, and then, upon the addition of an additional drop of waxy matrix 3, will have its viscosity drop significantly and/or switch from a solid or almost solid state into a fluid or almost fluid state (liquid or softened in particular). Hence, said surface treatment advantageously allows reducing the amount of fluidized waxy matrix 3 to be added to a considered amount of solid particles 2 for their mixture to loss its consistency, that is to say switches from a very viscous, solid or almost solid, state into a significantly less viscous, fluid or almost fluid, state. The surface treatments allowing causing a reduction of the capacity of absorption of the waxy matrix are known as such and vary according to multiple alternatives, the invention of course not being limited to a particular treatment. As a non-limiting example, the surface treatment of the solid particles 2 implemented in the context of the invention may be based on a treatment based on amino acids, for example N-acylamino acids such as the N-acyl-L-glutamic acid, and be advantageously in accordance with the teaching of the patent U.S. Pat. No. 4,606,914. For example, the surface treatment is based on a treatment based on amino acids in the form of metallic salts of N-acylamino acid, such as a salt made from sodium myristoyl glutamate and aluminum hydroxide. Of course, other surface treatments in accordance with the invention could be considered, and the surface treatment may for example be based on: a treatment implementing disodium myristoyl glutamate, advantageously as well as aluminum dimyristate and triethoxycaprylylsilane; a treatment implementing an alkoxysilane such as triethoxycaprylylsilane; a treatment in accordance with the teaching of the patent U.S. Pat. No. 6,482,441, a treatment implementing a fatty acid, a treatment implementing one or several phospholipid(s), a treatment implementing an olive oil hydrogenated ester, etc. For example, said solid particles 2 having undergone a surface treatment are formed by raw pigments (preferably more than 90 weight %), sodium myristoyl glutamate (preferably less than 10 weight %) and an aluminum hydroxide (preferably less than 10 weight %), according to a merely illustrative and non-limiting example. The surface treatment allowing causing a reduction of the capacity of absorption of the waxy matrix may further be formed by a combination of the different treatments listed hereinbefore. Advantageously, the surface treatments allowing causing a reduction of the capacity of absorption of the waxy matrix also allow increasing the hydrophobic nature of the treated solid particles 2, and/or improving their dispersability in an oil phase, in comparison with non-treated solid particles of the same kind.

Advantageously, said functional agent forms (strictly) more than 50 weight %, preferably more than 60 weight %, more preferably at least 70 weight %, even more preferably at least 80 weight %, even more preferably at least 85 weight % or even at least 90 weight % of said compound 1. Thus, preferably, at least 70 weight %, preferably at least 80 weight %, or at least 85 weight % of said compound 1, is formed by said solid particles 2. Such a high weight proportion of the functional agent (and therefore of the particles) is advantageously made possible thanks to said surface treatment. In turn, said waxy matrix preferably forms between 5 and 25 weight %, preferably between 7 and 22 weight %, more preferably between 15 and 20 weight %, of the compound 1. To sum up, advantageously, thanks to the surface treatment, a relatively small amount of the waxy matrix 3 is sufficient to serve as a support to a relatively large amount of solid particles 2.

Preferably, when it is fluidized and/or solubilized, the compound 1, and by extension the functional agent contained thereby (and more specifically said solid particles 2), could be dispersed or mixed in a homogeneous and stable manner within a cosmetic and/or dermatological composition. To sum up, thanks to the general principle of the invention, and in particular to the surface treatment, it is advantageously possible not only to obtain a compound 1 that is easy to handle comprising a large amount of the functional agent (at least 50 weight %, preferably at least 80 or even more preferably at least 85 weight %) and a small amount of the waxy matrix 3, but also to carry out, subsequently, an easy dispersion of the compound 1 within a cosmetic and/or dermatological composition during production to integrate said functional agent therein. Advantageously, the waxy matrix 3, and by extension the compound 1, serves as a support for the functional agent before redispersion thereof within a cosmetic and/or dermatological composition. Preferably, the redispersion of the compound 1 may be done by fluidification and therefore by heating of the compound 1 until making it fluid, to mix it more easily with cosmetically and/or dermatologically acceptable components which are themselves fluid, or by solubilization of the compound 1, preferably in the form of small solids (granulates in particles, for example pellets or sticks 4), possibly at low temperature (that is to say without heating), within cosmetically and/or dermatologically acceptable components which are fluid too.

In addition, the relatively small, or limited, amount of the waxy matrix 3 within said compound 1, as well as the nature of the latter, advantageously enables said compound 1 to be integrated to a wide range of cosmetic and/or dermatological compositions. In other words, the design of the compound 1 advantageously allows integrating said functional agent contained thereby within a cosmetic and/or dermatological composition, without, or almost without, any constraints with regards to the other compounds of the latter, that is to say without the need for modifying these other components forming said cosmetic and/or dermatological composition to adapt them to said compound 1. To sum up, the compound 1 of the invention could advantageously be integrated to a wide range of cosmetic and/or dermatological compositions.

Preferably, said waxy matrix 3 is liposoluble and/or insoluble or almost insoluble in water. Thus, the waxy matrix 3, which advantageously has physical characteristics close or similar to those of natural or synthetic waxes (and in particular silicone waxes), preferably has a lipophilic, liposoluble and/or hydrophobic nature. In particular, the waxy matrix 3 is dissolved in oil phases commonly used in the production of cosmetic and/or dermatological compositions. Advantageously, because of its small relative amount within the compound 1, the waxy matrix 3 is intended to relatively easily integrate the cosmetic and/or dermatological composition in which the compound is, in turn, intended to be integrated, preferably without significantly modifying the physical and/or chemical properties of said composition, and that being even more easily when said composition has a fatty or oil (and/or lipophilic) phase possibly within a water-in-oil type, for example water-in-silicone type, or alternatively oil-in-water type, emulsion.

Said compound 1 may possibly be intended to be redispersed so as to be part of a cosmetic and/or dermatological composition comprising only but an anhydride phase, preferably of the fat/oil/silicone type, said composition being for example a balm, a lipstick, etc.

Advantageously, said surface treatment also allows increasing the lipophilic and/or hydrophobic nature of the treated solid particles 2, in comparison with non-treated solid particles 2 of the same kind. Thus, the surface treatment confers on said solid particles 2 or reinforces in these a chemical affinity for fats and fatty matters and the same advantageously encompassing said waxy matrix 3. In particular, such a feature allows obtaining a better dispersion of the solid particles 2 within said waxy matrix 3 and/or a better dispersion of said compound 1 (and therefore of the solid particles 2 themselves) within a cosmetic and/or dermatological composition (in turn including in particular an oil phase or the same).

Figure 2:
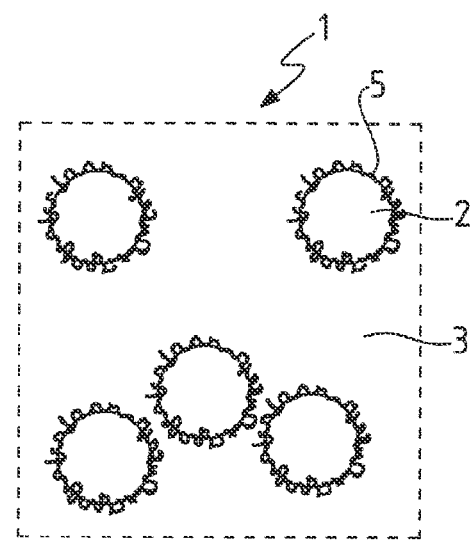
FIG. 2 schematically illustrates, on a microscopic or nanometric scale, a detail of the compound of FIG. 1.

Preferably, said surface treatment involves grafting of molecules 5 to the respective surface of said particles 2, as illustrated in FIG. 2. Still more preferably, said grafted molecules 5 comprise at least silicone chains, carbonated chains, natural or synthetic polymers, organic molecules, or titanium or silicon oxides. Thus, advantageously, said compound 1 comprises in particular said waxy matrix 3 and said treated particles 2, which are provided with and/or comprise said grafted molecules 5. Preferably, said particles 2 are evenly dispersed within the waxy matrix 3, at least partially thanks to said grafted molecules 5, the presence of which thus preferably reinforces the lipophilic and/or hydrophobic nature of the particles 2 and/or advantageously reduces their capacity of absorption of the waxy matrix 3.

Advantageously, said functional agent and said waxy matrix 3 form together at least 95 weight %, preferably at least 97 weight %, more preferably at least 99 weight %, even more preferably all, of said compound 1. Indeed, whether for making said compound 1 or for dispersing the latter within a cosmetic and/or dermatological composition, it is advantageously not necessary to integrate to the latter a component other than said waxy matrix 3 and said functional agent, although this still could be considered. Thus, preferably, the compound 1 does not comprise any surfactant, that is to say in particular it does not comprise any substance whose primary function is to lower the surface tension, or the compound 1 comprises such a substance but in a non-useful amount, negligible in weight with respect to the waxy matrix 3 and/or to the functional agent.

The invention also concerns, as such, according to a second aspect partially illustrated by an embodiment in FIG. 3, a method for producing a compound 1, which is preferably the compound 1 as described before (or hereinafter). Thus, the method of the invention allows producing a compound 1 comprising at least 50 weight % of a functional agent, preferably as mentioned hereinbefore, said compound 1 possibly comprising (strictly) more than 50 weight %, preferably (strictly) more than 60 weight %, more preferably at least 70 weight %, even more preferably at least 80 weight %, or 85 weight %, of said functional agent. Hence, the previous description regarding the compound 1 advantageously also applies to the manufacturing method according to the invention (and vice versa, the following description regarding the production method therefore also applies to the compound 1 according to the invention).

According to the invention, the production method comprises at least one step C of heating up a waxy matrix 3 in order to obtain a fluid matrix 3, said waxy matrix 3 being preferably that one already mentioned hereinbefore. In other words, during said heating step C, said waxy matrix 3 is heated up, for example using at least one resistance or by convection, until it is fluidized, that is to say molten or softened enough so as to no longer have the consistency of a solid, thereby forming a fluid waxy matrix 3. During said heating step, said waxy matrix 3 is advantageously heated up to a temperature equal to or higher than its melting and/or softening point. Thus, during the heating step, said waxy matrix 3 is heated for example up to a temperature comprised between 30 and 150° C. included, more preferably between 45 and 130° C. included, so as to be fluidized, or up to a temperature comprised between 55 and 95° C. included or between 55 and 150° C. included. Preferably, at low temperature, said waxy matrix 3 is thus substantially solid whereas at hot temperature, beyond a given temperature, it is substantially fluid. Preferably, the expression «fluid matrix» therefore refers to the waxy matrix 3 heated up until fluidification.

According to the invention, the method also comprises a step T (not illustrated) of treating solid particles 2 during which these undergo a surface treatment causing a reduction of the capacity of absorption of the fluid matrix 3 by the treated solid particles 2, in comparison with non-treated solid particles 2 of the same kind, said treated solid particles 2 forming said functional agent. Preferably, said solid particles 2 are as mentioned hereinbefore. In particular, as disclosed hereinbefore, said treatment step T advantageously involves grafting of molecules 5 to the respective surface of said particles 2 and/or an increase of the lipophilic and/or hydrophobic nature of the treated solid particles 2, in comparison with non-treated solid particles of the same kind.

Still according to the invention, the method further comprises a step D of dispersing said functional agent within said fluid matrix 3. Advantageously, said dispersion step D comprises at least one step M of mixing said treated particles 2 and of said waxy matrix 3, the latter could in particular be at low temperature, in a solid form, or at hot temperature, in a fluidized form.

According to the invention, said compound 1 is solid at room temperature and intended to be dispersed by fluidification and/or solubilization within a cosmetic and/or dermatological composition to integrate said functional agent therein, advantageously as described before.

Advantageously, the method further comprises a step B of grinding said solid particles 2 intended to reduce their average size. For example, upon completion of said grinding step B, said solid particles 2 have an average size substantially comprised between 10 nm and 500 μm, preferably between 100 nm and 100 μm.

Preferably, as illustrated in FIG. 3, said dispersion phase D comprises at least partially said grinding step B, so that during at least one portion of the latter, said fluid matrix 3 is mixed with said particles 2.

According to a particular embodiment of the invention, as illustrated in FIG. 3, the method further comprises a step E of extruding said compound 1 for the latter to be in the form of granulates, for examples pellets or sticks 4. Advantageously, the extrusion step E is carried out at hot temperature, said compound 1 having during this step a temperature comprised between 60 and 80° C.

Advantageously, after the dispersion step D, the method also comprises a cooling step F during which said compound 1 cools down to room temperature so as to form a solid.

According to an embodiment provided for illustrative and non-limiting purposes, illustrated in FIG. 3, the method successively involves:

said mixing step M, during which treated solid particles 2 and the waxy matrix 3 are mixed at low temperature, the matrix 3 being solid, at low temperature (room temperature), in the form of solid balls, whereas the particles 2 are in a coarse form, with a too large and therefore unacceptable grain-size, then said heating step C, during which the waxy matrix 3 is heated up and therefore fluidized, at the same time as the particles 2, which remain solid, then said grinding step B, during which the particles 2 are ground to an acceptable grain-size, while being/remaining closely mixed with the fluid matrix 3 which, in turn, undergoes a some kind of grinding, then a homogenization step H, during which the mixture formed by the ground particles 2 and the fluid matrix 3 is homogenized by any suitable means (stirring, blowing, shearing . . . ), then said extrusion step E, during which the hot mixture is compressed in order to cross a die 6 to obtain a long product in the form of a cylinder, then said cooling step F, during which the long product is progressively cooled down, then a cutting step S, during which the long product is cut, separated into several solids distinct of each other, such as preferably granulates, for example pellets or sticks 4, said dispersion step D herein comprising the mixing M, heating C, grinding B and homogenization H steps.

Advantageously, in particular according to this embodiment, the method involves the use of a twin-screw heater extruder 7, within which the steps disclosed hereinafter are carried out.

It is particularly advantageous to carry out said grinding step B so that the (average) grain-size of said solid particles 2 is reduced, and that said solid particles 2 being ground are mixed with the fluid matrix 3, which therefore also somehow undergoes said grinding. In other words, during said grinding step B, the particles 2 are ground in the presence of the fluid matrix 3. Thus, this grinding step B may be concomitant with said mixing step M. In this case, the grinding step B is particularly simple and easy to carry out, since all it needs is to grind the waxy matrix 3 mixed with the solid particles 2. Thanks to the grinding step B, the possible extrusion step E (which is preferably carried out afterwards) is greatly facilitated. Furthermore, this grinding step B may advantageously allow switching from a fine grinding of the solid particles 2 before mixing thereof with the waxy matrix 3, which avoids having to deal with very fine solid particles 2, therefore having a very pulverulent nature, with the drawbacks in terms of storage, safety and implementation resulting therefrom. Comparative tests have further demonstrated that the grinding step B would confer an excellent dispersability in fatty phase (for example, of a cosmetic composition) on examples of compounds 1 of the invention, in comparison with compounds that are equivalent yet not having been made by a method including said grinding step B and therefore having solid particles 2 whose grain-size remains substantially the same over the entire production process.

In order to highlight the improvement of the content of solid particles 2 within the compound 1, different examples of compounds 1, referred to as A1 to A3, in accordance with the invention, that is to say comprising solid particles 2 having undergone a surface treatment causing a reduction of the capacity of absorption of the waxy matrix, have been made, only for illustrative and non-limiting purposes. Examples of compounds referred to as A4 to A6 have also been made, but not in compliance with the invention, that is to say in this instance they comprise solid particles of the same kind as that of the solid particles of the examples of compounds A1 to A3, but without the surface treatment.

The examples of compounds A1 to A6 have been made according to Table 1, with regards to their respective solid particles (pigments in this instance).

TABLE 1

| Compounds | Solid particles (pigments) | Commercial, INCI, CAS and/or EINEC name of the pigments | Surface treatment of the solid particles (pigments) | Compound in accordance with the invention? |
|---|---|---|---|---|
| A1 | treated titanium dioxide (white pigments) | MiyoNAT VAA-White | yes | yes |
| A2 | treated red iron oxide | MiyoNAT VAA-Red | yes | yes |
| A3 | treated black iron oxide | MiyoNAT VAA-Black | yes | yes |
| A4 | titanium dioxide (white pigments) | CI 77891 13463-67-7 236-675-5 | none | no |
| A5 | red iron oxide | CI 77491 1309-37-1 215-168-2 | none | no |
| A6 | black iron oxide | CI 77499 1317-61-9 215-277-5 | none | no |

The invention also concerns, as such, according to a third aspect, a method for producing a cosmetic and/or dermatological composition, comprising a redispersion step R during which a compound 1, as described before, is added and then mixed with one or several cosmetically and/or dermatologically acceptable components. Advantageously, the previous description concerning the compound 1 and the method for producing a compound 1 also applies to the method for producing a composition according to the invention.

According to a first variant, said redispersion step R further comprises a step of solubilizing said compound 1 by one or more of said cosmetically and/or dermatologically acceptable components. Advantageously, said solubilization step comprises at least the solubilization (that is to say in particular the dispersion) of the compound 1 within a fatty phase (in particular oil) or a portion of said fatty phase of said cosmetic and/or dermatological composition.

According to a second variant, compatible with the first one described hereinbefore, said redispersion step R further comprises a fluidification step, in which said added compound 1 is heated up at least until fluidification. Said redispersion step R may also comprise said solubilization step and said fluidification step, for example one after another or, according to another example, concomitantly.

Preferably, for the redispersion step R and in particular for the solubilization step and/or for the fluidification step, one or more of said cosmetically and/or dermatologically acceptable components is/are substantially fluid at room temperature, thereby facilitating the redispersion of said compound 1 whether through solubilization thereof and/or through fluidification thereof.

In these examples, the solid particles of the compounds A4 to A6 consist of non-treated pigments, whose INCI, CAS and EINEC names are reported in Table 1. In these non-limiting examples, the solid particles 2 of the compounds A1 to A3 consist of treated pigments, that is to say (pigment type) solid particles 2 having undergone a surface treatment causing a reduction of the capacity of absorption of the waxy matrix. The respective commercial names (on the date of filing of the present patent application) of these treated pigments are reported in Table 1. The treated pigments of the compounds A1 to A3 are commercialized under their respective commercial names in particular by the company Miyoshi.

Each of these examples of compounds A1 to A6 has been prepared in several respective formulations, each containing one of the following respective proportions, in weight, of solid particles/waxy matrix: 40/60, 50/50, 60/40, 70/30, 80/20, and 85/15. Thus, 36 different formulations of these examples of compounds have been prepared, 18 of which are formulations of the examples of compounds 1 in accordance with the invention (A1 to 14), and 18 are not (A4 to A6). Of course, the implemented waxy matrix 3 is the same for all of the examples of compounds A1 to A6, and formed for example by polymethylsilsesquioxane. For example, the example of compound A1 refers to all of the formulations of this example of compound, namely six formulations with different respective proportions (mentioned hereinbefore), in weight, of solid particles/waxy matrix.

For example, the surface treatment of the pigments of the examples of compounds A1 to A3 may be carried out with a treatment based on amino acids, preferably in accordance with the teaching of the patent U.S. Pat. No. 4,606,914, the amino acids are in particular in the form of metallic salts of N-acylamino acid. Thus, for example, said surface treatment consists in coating raw, that is to say non-treated, solid particles (and in particular pigments) with 0.5 to 10 weight % of one or several metallic salts of N-acylamino acid, with respect to the weight of the raw solid particles. For example, the N-acylamino acid is a N-acyl-L-glutamic acid, whereas the metal consists for example of aluminum, magnesium, calcium, zinc or titanium. For example, the metallic salt of N-acylamino acid is made using sodium myristoyl glutamate and aluminum hydroxide. In particular, such a surface treatment may be used for the examples presented herein, for illustrative and non-limiting purposes, as well as in the rest of the description hereinbefore and hereinafter. Said surface treatment, in particular said treatment using metallic salts of N-acylamino acid, preferably increases the hydrophobic nature and the dispersability in oil of the treated solid particles 2 in comparison with the (non-treated) raw solid particles.

The examples of compounds A1 to A6 have been made by the method of the invention, herein including at least the already mentioned heating C, dispersion D and grinding B steps. Furthermore, these examples of compounds A1 to A6 have been subjected to said extrusion step E, and all are in the form of solid granulates at room temperature.

The results of the formulations of the examples of compounds are reported in Table 2. The mention «yes» refers to the success of a homogeneous compound formulation, that is to say in other words a homogeneous solid dispersion of pigments and of waxy matrix, preferably easy to extrude, and the mention «no» refers to the failure of a compound formulation, the obtained formulation then being generally heterogeneous, and possibly partially pulverulent, resulting from a poor distribution of the pigments and of the waxy matrix. As a general rule, the higher the content of pigments (that is to say of solid particles), the more difficult it would be to make a successful compound formulation.

TABLE 2

| | Pigments/matrix ratio (in weight) | | | | | |
|---|---|---|---|---|---|---|
| Compounds | 40/60 | 50/50 | 60/40 | 70/30 | 80/20 | 85/15 |
| A1 | yes | yes | yes | yes | yes | yes |
| A2 | yes | yes | yes | yes | yes | yes |
| A3 | yes | yes | yes | yes | yes | yes |
| A4 | yes | yes | no | no | no | no |
| A5 | yes | yes | no | no | no | no |
| A6 | yes | yes | no | no | no | no |

Thus, with the preparations of a solid dispersion of treated pigments A1 to A3, it has been possible to obtain homogeneous solid formulations containing all of the tested contents of pigments, that is to say herein 40 to 85 weight % of treated pigments.

However, with the formulations of the examples of compounds A4 to A6, it has been possible to obtain an acceptable results only for relatively low contents of pigments (40 and 50 weight % of non-treated pigments). Beyond 50 weight % of non-treated pigments, it has not been possible to obtain formulations of satisfactory homogeneous solid compounds, but only powdery and heterogeneous mixtures of pigments and of waxy matrix, which have a poor dispersability and could further complicate and even prevent the completion of said extrusion step E.

According to the aforementioned results, it has been demonstrated that the surface treatment of the solid particles 2 (pigments in these particular examples), in the examples of compounds 1 of the present invention, allowed significantly increasing the concentration of said pigment solid particles in the waxy matrix 3.

In order to highlight the excellent (re)dispersability of the compound 1, different examples of compounds 1, referred to as A7 to A12, in accordance with the invention, have been made, only for illustrative and non-limiting purposes, and are reported in Table 3.

TABLE 3

| Compound | Solid particles (pigments) - Commercial name | Waxy matrix | Pigments/ matrix ratio (in weight) |
|---|---|---|---|
| A7 | treated titanium dioxide (MiyoNAT VAA-White) | wax | 85/15 |
| A8 | treated red iron oxide (MiyoNAT VAA-Red) | wax | 85/15 |
| A9 | treated black iron oxide (MiyoNAT VAA-Black) | wax | 85/15 |
| A10 | treated titanium dioxide (white pigments) (MiyoNAT VAA-White) | silicone resin | 85/15 |
| A11 | treated red iron oxide (MiyoNAT VAA-Red) | silicone resin | 85/15 |
| A12 | treated black iron oxide (MiyoNAT VAA-Black) | silicone resin | 85/15 |

The treated pigments (which therefore consist of solid particles having undergone a surface treatment causing a reduction of the capacity of absorption of the waxy matrix) of the compounds A7 to A12 reported in Table 3 are the same as those of the compounds A1 to A3. The term «wax» of the compounds A7 to A9 in Table 3 refers, for example, to an olive oil ester wax, whereas the silicone resin of the compounds A10 to A12 in Table 3 is, for example, formed by polymethylsilsesquioxane.

The examples of compounds A7 to A12 have been made by the method of the invention, herein including at least the already mentioned heating C, dispersion D and grinding B steps. Furthermore, these examples of compounds A7 to A12 have undergone said extrusion step E, and all are in the form of solid granulates at room temperature. The solid particles 2 (herein different pigments) of these examples of compounds A7 to A12, have undergone a surface treatment in accordance with the invention, for example using one or several metallic salt(s) of N-acylamino acid(s), preferably in accordance with the teaching of the patent U.S. Pat. No. 4,606,914.

The (re)dispersability of the examples of compounds A7 to A12 has been assessed by mixing each of them, separately, in different types of liquid fatty bodies (a linear or branched alkane type apolar oil, or linear or branched ester type polar oil, or triglyceride type polar oil, or demethicone type linear silicone oil, a cyclopentasiloxane type cyclic silicone oil, or methyl trimethicone type branched silicone oil), according to a ratio, in weight, of one portion of solid dispersion of pigment in two portions of liquid fatty bodies. Thus, each of these liquid fatty bodies may be intended to form a fatty phase or a portion of a fatty phase of a cosmetic and/or dermatological composition. In other words, the assessment of the dispersability of the examples of compounds A7 to A12 in these different fatty bodies allows assessing the ability/the ease of homogeneous dispersion of the examples of compounds A7 to A12 within a respective cosmetic and/or dermatological composition.

The dispersability of the examples of compounds A7 to A12 in a respective liquid fatty body has been achieved by means of relatively common mixing equipment (such as a deflocculator turbine, at 3300 rpm for 5 to 15 min, or a disperser Ultra-turrax®, at 8000 rpm, for 5 to 15 min). No step of fine grinding of pigments alone, such as for example in a three-cylinder, has been performed prior to making of the examples of compounds A7 to A12.

The examples of compounds A7 to A9 have been mixed with the liquid fatty bodies at hot temperature (between 60 and 80° C.) to form respective mixtures M7 to M9. The examples of compounds A10 to A12 have been mixed with the liquid fatty bodies at room temperature (25° C.) to form respective mixtures M10 to M12.

The dispersability (that is to say the distribution homogeneity) of the examples of compounds A7 to A12 within their respective liquid fatty bodies has been assessed by observation of the mixtures M7 to M12 with optical microscopy, spreading between two glass plates and spreading over a grindometer (also called Hegman gauge) at 100 μm and 25 μm, and comparison with the compositions M7' to M12' including pigments and liquid fatty bodies of the same kind (but non-treated in the case of pigments) and at the same proportions as the mixtures A7 to A12. However, the pigments of the compositions M7' to M12' have been made with fine grinding equipment (grinding with a three-cylinder for example) and dispersed directly in the pulverulent form within their respective liquid fatty bodies to form said compositions M7' to M12', without any intermediate dispersion in a waxy matrix.

The results of the observations described hereinbefore show that the mixtures M7 to M12, whose pigments have undergone a surface treatment and have then been integrated within examples of compounds A7 to A12 (in turn integrated within the mixtures M7 to M12), had the same grinding fineness (particle size, homogeneity of the dispersion) as the mixtures M7' to M12', whose pigments have undergone a fine grinding, with a three-cylinder for example, but no surface treatment or integration within a compound 1 of the invention intended to be redispersed.

According to the aforementioned results, it has been demonstrated that the solid particles 2 (herein pigments) present in the examples of solid compounds A7 to A12 in accordance with the present invention have been dispersed uniformly in the liquid fatty bodies (considered as portions of a cosmetic and/or dermatological composition) at a high content (in weight) of solid particles 2, and that being so over a limited time period (normal mixing duration). Consequently, the compound 1 of the present invention allows obtaining an excellent ease of redispersion of solid particles 2, and in particular of pigments, within a cosmetic and/or dermatological composition, and in particular within a fatty (oil) phase of a cosmetic and/or dermatological composition.

Examples of cosmetic and/or dermatological compositions, made according to the composition production method of the invention, each integrating at least one compound 1 in accordance with the invention, are described hereinafter, for illustrative and non-limiting purposes:

Composition M20: skin foundation made by water-in-silicone emulsion, having the following composition (in weight):
Fatty phase
Surfactant of the PEG-10 dimethicone type or of the PEG-20 diethicone type or of the PEG-9 lauryl polydimethylsiloxyethyl dimethicone type: 3.00%
Dispersion of disteardimonium hectorite and of propylene carbonate: 1.00%
Cyclopentasiloxane: 17.25%
Alkane type apolar oil or ester type polar oil or triglyceride type polar oil or dimethicone type linear silicone oil or cyclopentasiloxane type cyclic silicone oil: 10.00%
Compound 1 in accordance with the invention, selected amongst the examples of compounds A7 to A12: 10.00%
Aqueous phase
Magnesium sulfate: 0.75%
Xanthan gum: 0.15%
Butylene glycol: 5.00%
Preservative: 0.75%
Demineralized water: Q.S.
Composition M21: water-in-oil emulsion, having the following composition (in weight):
Fatty phase
Surfactant of the polyglyceryl-3-diisostearate type: 3.00%
Waxes: 2.00%
Glyceryl behenate: 1.00%
Isononyl isononanoate oil: 10.00%
Alkane type apolar oil or ester type polar oil or triglyceride type polar oil or dimethicone type linear silicone oil or cyclopentasiloxane type cyclic silicone oil: 5.00%
Compound 1 in accordance with the invention, selected amongst the examples of compounds A7 to A12: 10.00%
Aqueous phase
Sodium chloride: 1.50%
Magnesium sulfate: 1.50%
Xanthan gum: 0.20%
Butylene glycol: 3.00%
Preservative: 0.30%
Demineralized water: Q.S.
Composition M22: skin foundation made by water-in-oil emulsion, at low temperature, having the following composition (in weight):
Fatty phase
Surfactant of the polyglyceryl-3-polyricinoleate type: 8.00%
Dispersion of disteardimonium hectorite and of propylene carbonate: 5.00%
Alkane type oil: 13.70%
Amorphous silica type texturing agent: 5.00%
Preservative: 1.00%
Compound 1 in accordance with the invention, selected amongst the examples of compounds A10 to A12: 10.00%
Aqueous phase
Sodium chloride: 1.00%
Glycerin: 3.00%
Xanthan gum: 0.30%
Demineralized water: Q.S.
Composition M23: anhydrous skin foundation in stick, having the following composition (in weight):
Fatty phase
Waxes: 70.00%
Alkane type apolar oil or ester type polar oil or triglyceride type polar oil or dimethicone type silicone oil or cyclopentasiloxane type silicone oil: 20.00%
Compound 1 in accordance with the invention, selected amongst the examples of compounds A7 to A9: 10.00%.
Composition M24: lipstick, having the following composition (in weight):
Fatty phase
Waxes: 70.00%

Alkane type apolar oil or ester type polar oil or triglyceride type polar oil or dimethicone type silicone oil or cyclopentasiloxane type silicone oil: 14.50%

Amorphous silica type texturing agent: 5.00%

Tocopherols: 0.50%

Compound 1 in accordance with the invention, selected amongst the examples of compounds A7 to A9: 10.00%.

For each of the examples of compositions M20 to M24, the compound 1 has been mixed with the fatty phase, either at room temperature (about 25° C.) for the examples of compounds A10 to A12, or at hot temperature (60-80° C. or 75-85° C.) for the examples of compounds A7 to A9. In these embodiments of compositions, each compound 1 is always mixed firstly with the respective fatty phase, using a deflocculator turbine and/or a rotor-stator.

The stability of the examples of compositions M20 to M22 (which consist of emulsions) has been monitored over two months, at room temperature (25° C.), at 40° C. and at 50° C. Their respective viscosities have also been monitored over two months at room temperature (25° C.). No significant change has been observed. Hence, the compound 1 of the invention not only allows for an excellent redispersability of the solid particles 2 within a cosmetic and/or dermatological composition, but what is more it does not negatively impact the latter with regards to its stability over time.

The homogeneity of the examples of compositions M20 to M24 has been assessed by observation of these with optical microscopy, spreading between two glass plates and spreading over a grindometer (also called Hegman gauge) at 100 μm and 25 μm, and comparison with examples of compositions M20' to M24' including solid particles 2 (pigments of the examples of compounds A7 to A12) and other components of the same kind (but non-treated in the case of the solid particles 2) and at the same proportions as the examples of compositions M20 to M24. The pigments of the examples of compositions M20' to M24' have been made with fine grinding equipment (grinding with a three-cylinder for example) and dispersed in the pulverulent form within their respective liquid fatty bodies to form said examples of compositions M20' to M24', without any intermediate dispersion in a waxy matrix.

The results of the observations described hereinbefore show that the examples of compositions M20 to M24, prepared from the examples of compounds A7 to A12 of the invention, had the same grinding fineness (particle size, homogeneity of the dispersion) as the examples of compositions M20' to M24', whose pigments have undergone a fine grinding, with a three-cylinder for example, but no surface treatment or integration within a compound 1 of the invention intended to be redispersed. In other words, each of the examples of cosmetic compositions M20 to M24, each containing a respective compound 1 according to the invention including, in turn, solid particles 2, had the same emulsion fineness (particle size, homogeneity of the dispersion) as if their solid particles have been ground finely and for a long time in a three-cylinder, without the passage through a compound 1 of the invention or surface treatment, and introduced directly in a pulverulent form within the examples of compositions.

INDUSTRIAL APPLICABILITY

Thus, the invention allows obtaining a compound 1 including a large content of a functional agent and facilitating the transport, storage and handling of the latter.

The invention claimed is:

1. A compound (1) comprising at least 50 weight % of a functional agent, characterized in that it also comprises a waxy matrix (3) within which said functional agent is dispersed, said compound (1) being solid at room temperature and intended to be dispersed by fluidification and/or solubilization within a cosmetic and/or dermatological composition to integrate said functional agent therein, said functional agent being formed by solid particles (2) having undergone a surface treatment causing a reduction of the capacity of absorption of the waxy matrix (3) by said treated solid particles (2), in comparison with non-treated solid particles of the same kind.

2. The solid compound (1) according to claim 1, characterized in that said surface treatment also allows increasing the lipophilic and/or hydrophobic nature of the treated solid particles (2), in comparison with non-treated solid particles of the same kind.

3. The solid compound (1) according to claim 1, characterized in that said surface treatment involves grafting of molecules (5) at the respective surface of said particles (2).

4. The compound (1) according to claim 3, characterized in that said grafted molecules (5) comprise at least silicone chains, carbonated chains, natural or synthetic polymers, organic molecules, or titanium or silicon oxides.

5. The compound (1) according to claim 1, characterized in that said waxy matrix (3) comprises at least one natural, mineral and/or synthetic wax, a fatty body solid at room temperature derived from the fractioning of at least one natural and/or synthetic oil(s), a natural and/or synthetic resin, a silicone or silicone polymer wax, or a mixture of these.

6. The compound (1) according to claim 1, characterized in that said waxy matrix (3) comprises a polymethylsilsesquioxane.

7. The compound (1) according to claim 1, characterized in that said solid particles (2) have an average size comprised between 10 nm and 500 μm.

8. The compound (1) according to claim 1, characterized in that said solid particles (2) comprise at least organic and/or mineral pigments, organic and/or mineral charges, composite and/or biocomposite materials, or a mixture of these.

9. The compound (1) according to claim 1, characterized in that said waxy matrix (3) is liposoluble and/or insoluble in water.

10. The compound (1) according to claim 1, characterized in that said waxy matrix (3) has a melting point and/or a softening point comprised between 3° and 150° C. included.

11. The compound (1) according to claim 1, characterized in that it is in the form of granulates comprising pellets or sticks (4), obtained by extrusion.

12. The compound (1) according to claim 1, characterized in that said functional agent forms at least 70 weight % of said compound (1).

13. The compound (1) according to claim 1, characterized in that said functional agent and said waxy matrix (3) form together at least 95 weight % of said compound (1).

14. The compound (1) according to claim 1, characterized in that it does not comprise any surfactant.

15. The compound (1) according to claim 6, characterized in that said waxy matrix (3) is formed by said polymethylsilsesquioxane.

16. The compound (1) according to claim 7, characterized in that said solid particles (2) have an average size comprised between 100 nm and 100 μm.

17. The compound (1) according to claim 10, characterized in that said waxy matrix (3) has a melting point and/or a softening point comprised between 45 and 130° C. included.

18. The compound (1) according to claim 12, characterized in that said functional agent forms at least 80 weight % of said compound (1).

19. The compound (1) according to claim 13, characterized in that said functional agent and said waxy matrix (3) form together at least 97 weight % of said compound (1).

20. The compound (1) according to claim 19, characterized in that said functional agent and said waxy matrix (3) form together at least 99 weight % of said compound (1).

21. The compound (1) according to claim 20, characterized in that said functional agent and said waxy matrix (3) form together all of said compound (1).

* * * * *